United States Patent
Cakmak et al.

(10) Patent No.: US 9,855,426 B2
(45) Date of Patent: Jan. 2, 2018

(54) ELECTRO-STIMULATION DEVICE

(71) Applicant: Koc Universitesi, Sariyer, Istanbul (TR)

(72) Inventors: Yusuf Ozgur Cakmak, Istanbul (TR);
Hakan Urey, Istanbul (TR); Selim Olcer, Istanbul (TR); Kaan Aksit, Istanbul (TR)

(73) Assignee: KOC Universitesi, Istanbul (TR)

( * ) Notice: Subject to any disclaimer, the term of this patent is extended or adjusted under 35 U.S.C. 154(b) by 5 days.

(21) Appl. No.: 14/979,069

(22) Filed: Dec. 22, 2015

(65) Prior Publication Data

US 2016/0106982 A1  Apr. 21, 2016

Related U.S. Application Data

(63) Continuation-in-part of application No. PCT/IB2013/055327, filed on Jun. 28, 2013.

(51) Int. Cl.
| | |
|---|---|
| *A61N 1/36* | (2006.01) |
| *A61N 1/05* | (2006.01) |
| *A61N 1/372* | (2006.01) |
| *A61N 1/04* | (2006.01) |

(52) U.S. Cl.
CPC ....... *A61N 1/36067* (2013.01); *A61N 1/0526* (2013.01); *A61N 1/36003* (2013.01); *A61N 1/36135* (2013.01); *A61N 1/37247* (2013.01); *A61N 1/0452* (2013.01)

(58) Field of Classification Search
None
See application file for complete search history.

(56) References Cited

U.S. PATENT DOCUMENTS

| | | | | |
|---|---|---|---|---|
| 4,690,144 A | * | 9/1987 | Rise | ........... A61N 1/36014 607/59 |
| 2008/0249594 A1 | | 10/2008 | Dietrich et al. | |
| 2009/0306484 A1 | * | 12/2009 | Kurtz | ........... A61B 5/0059 600/300 |

(Continued)

FOREIGN PATENT DOCUMENTS

| | | |
|---|---|---|
| EP | 1671670 A1 | 6/2006 |
| WO | WO 2010/048261 A1 | 4/2010 |

OTHER PUBLICATIONS

International Search Report of the International Searching Authority, dated Jan. 7, 2014, pp. 1-3, issued in International Application No. PCT/IB2013/055327, European Patent Office, Rijswijk, The Netherlands.

(Continued)

*Primary Examiner* — Ankit D Tejani
(74) *Attorney, Agent, or Firm* — Brinks Gilson & Lione

(57) ABSTRACT

An electro-stimulation device where the supplementary motor area, premotor area and/or subthalamic nucleus is stimulated extracranially via intrinsic auricular muscles and the stimulation intensity of the supplementary motor area, premotor area and/or subthalamic nucleus is changed with the intensity of the tremors. The electro-stimulation device comprises; at least two primary electrodes which enables sending and receiving electric signals, at least one control unit which produces stimulating signals for reducing involuntary resting activities such as tremors and enables these signals to be sent to/received from primary electrodes.

32 Claims, 3 Drawing Sheets

(56) References Cited

U.S. PATENT DOCUMENTS

| | | | |
|---|---|---|---|
| 2010/0217348 A1* | 8/2010 | DiLorenzo | A61N 1/3605 607/45 |
| 2011/0093049 A1* | 4/2011 | Hinrichsen | A61H 39/002 607/72 |
| 2011/0208265 A1* | 8/2011 | Erickson | A61N 1/37247 607/46 |
| 2012/0078323 A1* | 3/2012 | Osorio | A61N 1/36064 607/45 |
| 2013/0079862 A1 | 3/2013 | Ellrich | |
| 2013/0123568 A1* | 5/2013 | Hamilton | A61N 1/36003 600/13 |
| 2013/0123684 A1* | 5/2013 | Giuffrida | A61N 1/36067 604/65 |

OTHER PUBLICATIONS

International Preliminary Report on Patentability (PCT Article 36 and Rule 70), dated Mar. 9, 2015, pp. 1-19, issued in International Application No. PCT/IB2013/055327, European Patent Office, Munich, Germany.

Intention to Grant, dated Jun. 13, 2017, pp. 1-46, issued in International Application No. PCT/IB2013/055327, European Patent Office, Munich, Germany.

* cited by examiner

ELECTRO-STIMULATION DEVICE

CROSS-REFERENCE TO RELATED APPLICATION

This application is a continuation-in-part of PCT Patent Application Serial Number PCT/IB2013/055327 filed Jun. 28, 2013, which is incorporated by reference.

BACKGROUND

The present disclosure relates to an electro-stimulation device where the supplementary motor area, premotor area and/or subthalamic nucleus are stimulated extracranially.

Stimulation of the subthalamic nucleus and as a consequence, activations of the supplementary motor areas and premotor areas and normalization of the abnormal involuntary resting activity in the motor system are the primary targets of the deep brain stimulation devices. Abnormal involuntary resting activity such as tremors may be caused by conditions or medicines that affect the nervous system, including Parkinson's disease, liver failure, alcoholism, mercury or arsenic poisoning, lithium, and certain antidepressants. Rigidity, bradykinesia and dyskinesia are other symptoms of the Parkinson's disease besides tremors.

Current applications to stimulate subthalamic nucleus include intracranial electrode placement, which is called deep brain stimulation. The process of deep brain stimulation of the subthalamic nucleus requires a neurosurgery, which is an extremely invasive intervention for the Parkinson's patient. Further, surgical device applications are likely to have side effects. Moreover, the battery of the stimulator is placed under the thorax skin while the electrodes inserted into the brain tissue and the wires goes under the skin. The frequency and the intensity of these stimulators may be altered wirelessly with an external unit.

BRIEF DESCRIPTION

An aspect of an embodiment is to provide an electro-stimulation device where the supplementary motor area, premotor area and/or subthalamic nucleus is stimulated extracranially.

Another aspect of an embodiment is to provide an electro-stimulation device where the supplementary motor area, premotor area and/or subthalamic nucleus is stimulated via auricular muscles.

Another aspect of an embodiment is to provide an electro-stimulation device where the stimulation intensity of the supplementary motor area, premotor area and/or subthalamic nucleus is changed with the intensity of the tremors.

BRIEF DESCRIPTION OF THE DRAWINGS

An electro-stimulation device is illustrated in the attached figures, where.

Figure 1:
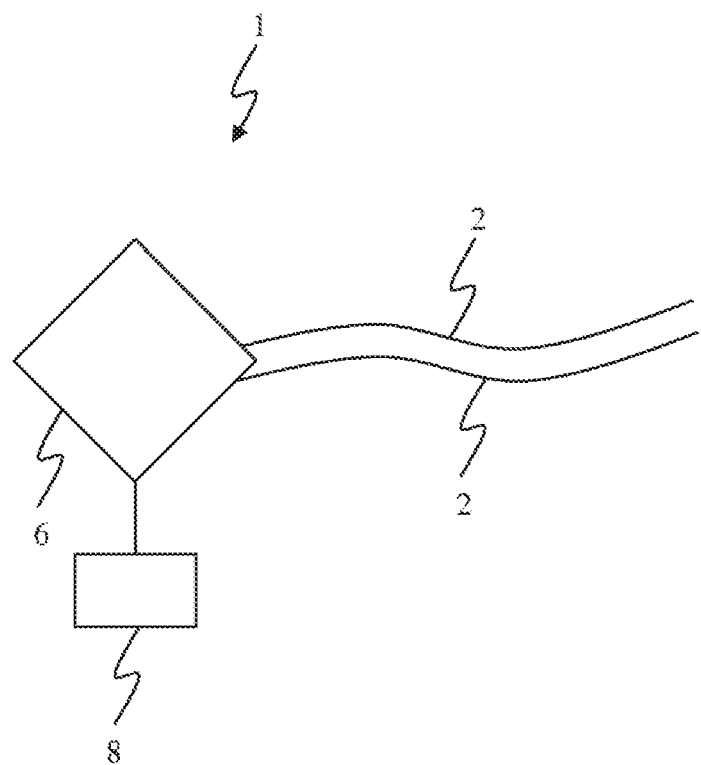
FIG. 1 is the schematic view of one embodiment of an electro-stimulation device.
Figure 2:
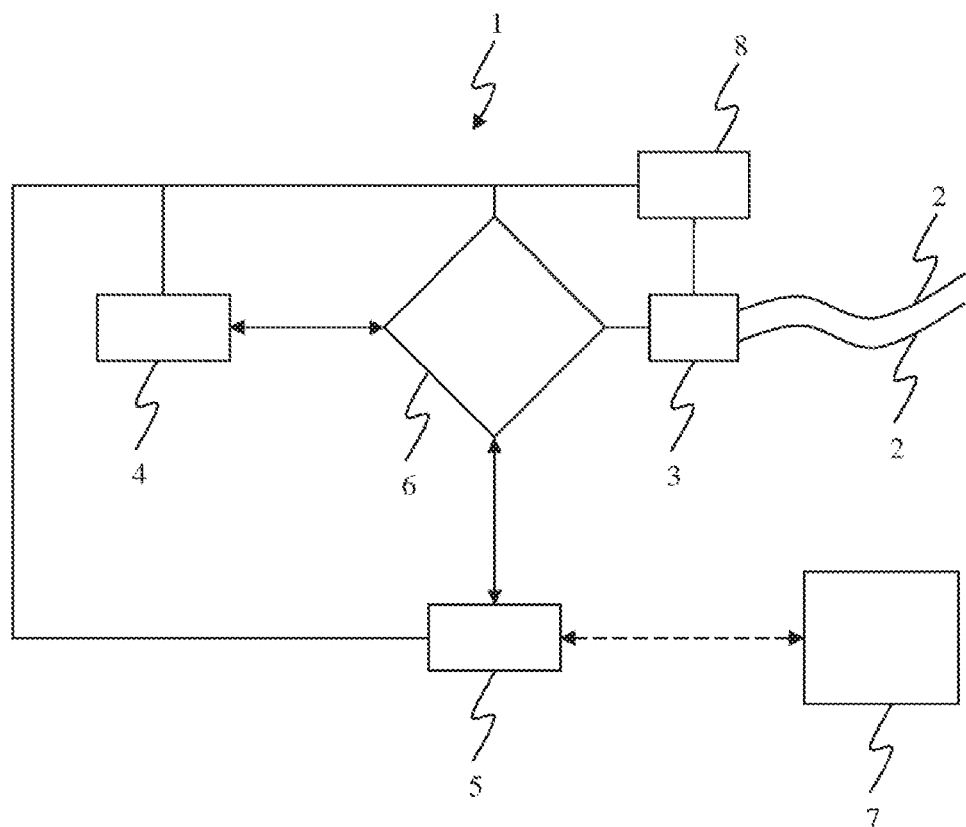
FIG. 2 is the schematic view of another embodiment of an electro-stimulation device.
Figure 3:
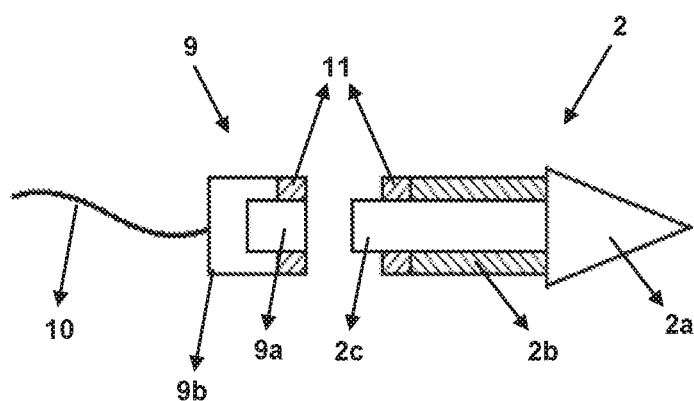
FIG. 3 is a side cross-sectional view of an electrode in the form of an acupuncture needle.

Elements shown in the figures are numbered as follows:
1. Electro-stimulation device
2. Primary Electrode
2a. Tip
2b. Insulating Sleeve
2c. Base
3. Driving circuit
4. Sensing unit
5. Communication unit
6. Control unit
7. Remote unit
8. Ground electrode
9. Connection Element
9a. Socket
9b. Cover
10. Connection Line
11. Magnet

DETAILED DESCRIPTION

The inventive electro-stimulation device (1) essentially comprises;
at least two primary electrodes (2) which enables sending and receiving electric signals and that are adapted to be attached to intrinsic auricular muscles such as helicis major, helicis minor, tragicus, anti-tragicus etc,
at least one control unit (6) which produces stimulating signals for reducing involuntary resting activities such as tremors and enables these signals to be sent to/received from the primary electrodes (2),
a ground electrode (8) which provides closing of the loop for the electrical current by providing an electrical path to the negative terminal of a power supply In one embodiment, the electro-stimulation device (1) comprises at least one driving circuit (3) which provides voltage or current amplified signal from the control unit (6) to the primary electrodes (2).

In one embodiment, the electro-stimulation device (1) comprises at least one sensing unit (4) configured to receive data from a patient. The sensing signals and the stimulating signals may be carried via separate or the same primary electrodes (2). In a preferred embodiment, sensing signals and the stimulating signals may be carried via the same primary electrodes (2). Different time slots may be allocated for sensing signals and the stimulating signals, thus multiplexing said sensing signals and said stimulating signals. Another method for arranging the sensing signals and the stimulating signals is to filter out the stimulating signals that are generated by the control unit (6). It should be known that different methods for multiplexing the said sensing signals and said stimulating signals, such as space-division multiplexing, time-division multiplexing, code-division multiplexing etc., could also be utilized. The methods for multiplexing the said sensing signals and said stimulating signals are not limited to those disclosed above.

In one embodiment, the electro-stimulation device (1) comprises at least one communication unit (5) which enables realizing communication with other additional devices, such as remote control units, computers, measurement units, etc.

In one embodiment, the electro-stimulation device (1) comprises at least one remote unit (7) which enables receiving data from the control unit (6) and/or changing settings of the control unit remotely.

In a preferred embodiment, the electro-stimulation device (1) comprises,
at least two primary electrodes (2) which enables sending and receiving electric signals,
at least one driving circuit (3) which enables providing power higher than the power limit of the control unit (6) to the primary electrodes (2) by controlling a power supply, at least one sensing unit (4) which enables receiving data from a patient, at least one communication unit (5) which enables realizing communication with other additional devices at least one control unit (6) which enables electric signals to be sent to/received from primary electrodes (2), controlling the driver (3), receiving signals from the sensing unit (4) and controlling the communication unit (5), at least one remote unit (7) which enables receiving data from the control unit (6) and/or changing settings of the control unit remotely, In the preferred embodiment, the electro-stimulation device (1) comprises at least two primary electrodes (2), which enable sending and receiving electric signals in order to stimulate especially supplementary motor area, premotor area and/or subthalamic nucleus. In the preferred embodiment, these primary electrodes (2) are attached to intrinsic auricular muscles such as helicis major, helicis minor, tragicus, anti-tragicus etc. In this embodiment, the stimulating signal for stimulating the supplementary motor area, premotor area and/or subthalamic nucleus is produced by the control unit (6) and fed directly to the primary electrodes (2). In another embodiment, multiple primary electrodes (2) are used on the same part or different parts of the body. In a preferred embodiment, one electro-stimulation device may be placed on the aforementioned locations on the left ear and the other one on the right ear. The ground electrode (8) closes the loop for the electrical current by providing an electrical path to the negative terminal of the power supply. It may be a small conductive contact or a pad with an area of several square centimeters. The ground electrode (8) connection may be at the back of the ear, neck, scalp, or other places in the proximity of the primary electrode (2).

In one embodiment, the electro-stimulation device (1) comprises at least one sensing unit (4) which enables making measurements related to the status of the patient. The sensing unit (4) may be a camera, which enables receiving images from the patient and hence enabling visually monitoring the symptoms such as tremors. The received images are then processed by image processing techniques and information such as the intensity of the tremors is acquired.

In one embodiment, one of the at least one sensing unit (4) is an accelerometer. In this embodiment, the sensing unit (4) is attached to the limb, the activity of which is wanted to be known. In this embodiment, sensing unit (4) is used to sense the intensities of disturbances by measuring the acceleration of the limb, to which the sensing unit (4) is attached. Upon measuring the disturbance level, the stimulating signal is adjusted so that it may compensate for said disturbance level. In this embodiment the measurement of the disturbance level is conducted periodically so that the stimulating signal may be adapted to the changing status of the patient. In this embodiment, the sensing unit (4) may utilize a dedicated control unit and a dedicated communication unit in order to transfer the results of the measurements to the control unit (6) wirelessly. The adjustments to the said signal can be induced by changing the amplitude, frequency, pulse width, and pulse shape such as the harmonic content of the periodic pulses, or the phase between the electro-stimulating device if more than one stimulator is used.

In one embodiment, the sensing unit (4) is a signal receiver, which utilizes the primary electrodes (2) in order to receive the signals passing by the muscles to which these primary electrodes (2) are attached. In this embodiment, sensing unit (4) is used to sense the intensity of disturbances by measuring the signals during a resting period. Upon measuring the disturbance level, the stimulating signal is adjusted so that it may compensate the said disturbance level. In this embodiment the measurement of the disturbance level is conducted periodically so that the stimulating signal may be adapted to the changing status of the patient.

In a preferred embodiment, the electro-stimulation device (1) comprises at least one communication unit (5) which enables communication with other devices such as remote control units, computers, measurement units etc. The communication unit (5) may utilize communication standards including but not limited to IR, USB, firewire, ethernet, IEEE802.11, Bluetooth, RF communication interface, RS-232, RS-422, RS-485, SPI (serial peripheral interface) i2c, as well as proprietary interfaces and/or protocols and such.

In one embodiment, the signal for stimulating the supplementary motor area, premotor area and/or subthalamic nucleus is produced by the control unit (6) and the signal is used to trigger a driving circuit (3), instead of being fed directly to the primary electrodes (2). This driving circuit enables driving powers greater than control unit (6) is able provide, from a power source. In this application, the driven power is fed to the primary electrodes (2) by the driving circuit (3).

In one embodiment, the sensing unit (4) comprises a dedicated control unit and a dedicated communication unit. In this embodiment, the sensing unit (4) is not directly attached to the primary control unit (6) and instead, it is linked to the primary control unit (6) via the dedicated communication unit and the primary communication unit (5). In this embodiment, the sensing unit (4) processes the acquired data using the dedicated control unit and sends the resulting data to the primary control unit (6) via the link between the dedicated communication unit and the primary communication unit (5). The primary control unit (6) receives the sent data via the primary communication unit (5).

In one embodiment, the remote unit (7) is used for changing working parameters of the control unit (6). In this embodiment, the measurements conducted by the sensing unit (4) may be acquired by the remote unit (7) as well. The remote unit may utilize a display unit, which may be used to display the data acquired from the control unit (6) directly on the remote unit (7). The remote unit (7) may also utilize interfaces including but not limited to USB, RS-232, RS-485, bluetooth and such, in order to provide connectivity with terminals including but not limited to desktop computers, portable computers, handheld computers, tablet computers, smart phones and proprietary units. In this embodiment, the working parameters of the control unit (6) may be monitored and changed via these terminals. It should be clearly understood that the remote unit (7) utilizes dedicated communication interfaces in order to communicate with the control unit (6). These interfaces include, but they are not limited to, IR, USB, firewire, ethernet, IEEE802.11, Bluetooth, RF communication interface, RS-232, RS-422, RS-485, SPI (serial peripheral interface) i2c, as well as proprietary interfaces and/or protocols and such.

In a preferred embodiment, the stimulating signal produced by the control unit (6) has the voltage of 0V-15V and the frequency of 2 Hz-200 Hz. The voltage and the frequency of the stimulating signal may be automatically changed depending on the situation of the patient by the control unit (6) or it may be remotely changed via the remote unit (7) by an authorized user such as a physician, upon evaluating the situation of the patient.

In a preferred embodiment of the present application, at least one of said electrodes (2) are in the form of an acupuncture needle. Preferably, each of said acupuncture needle electrodes (2) comprise an insulating sleeve (2b). Said insulating sleeve (2b) surrounds the acupuncture needle electrode (2), except for the tip (2a) of the electrode (2). In this embodiment, electrodes (2) are pricked on the auricular skin and tips (2a) of the electrodes (2) reach said intrinsic auricular muscles. Said insulating sleeve (2b) prevents signals produced by the control unit from reaching the auricular skin, thus ensures that the signals are directly transmitted to the intrinsic auricular muscles. Preferably, one section said tip (2a) is slightly thicker than the insulating sleeve (2b). Said thicker section prevents tip (2a) from disconnecting the intrinsic auricular muscles.

In another preferred embodiment of the present application, said electrodes (2) are detachable from the driving circuit (3). In this embodiment, electro-stimulation device (1) comprises at least one connection element (9), which is connected to said driving circuit (3) via connection lines (10) and which is detachably connected to at least one electrode (2). Said connection element (9) comprises at least one cover (9b), preferably made from an insulating material, and at least one socket (9a), suitable for receiving a base (2c) portion of the electrode (2). In this embodiment, electro-stimulation device (1) further comprises a pair of magnets (11), one of which is placed on connection element (9) and one other is placed on the electrode (2). Said pair of magnets (11) ensures that connection element (9) is securely connected to the electrode (2). According to this embodiment, electrodes (2) are implanted to the ear of the patients such that tip (2a) of the electrode (2) is in connection with said intrinsic auricular muscles and patients can attach/detach said connection element (9) to the electrode whenever they want.

The methods, devices, processing, and logic described above may be implemented in many different ways and in many different combinations of hardware and software. For example, all or parts of the implementations, such as control units, sensing units, communication units, remote units and display units, may be circuitry that includes an instruction processor, such as a Central Processing Unit (CPU), a microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

We claim:

1. An electro-stimulation device adapted to stimulate at least one of a supplementary motor area, a premotor area, or a subthalmic nucleus via auricular muscles comprising:
   at least two primary electrodes configured to send and receive electric signals;
   at least one control unit configured to at least one of send electric signals or receive electric signals from the primary electrodes; and
   a ground electrode configured to close a loop for an electrical current by providing an electrical path to a negative terminal of a power supply;
   wherein the control unit is configured to produce stimulating signals which are sent to the at least two primary electrodes, the stimulating signals having a frequency that is dynamically adjustable between 2-200 Hz for reducing abnormal resting activities;
   wherein the electrodes are adapted to be attached to intrinsic auricular muscles;
   at least one remote unit configured to at least one of receive data from the control unit or change settings of the control unit remotely; and
   at least one sensing unit configured to receive abnormal resting activity data from a patient comprising at least one of tremors, rigidity and motion;
   wherein the control unit is further configured to monitor a status of a patient by periodic evaluation of the abnormal resting activity data provided by the sensing unit, and by periodic evaluation of characteristics of the stimulating signals, said characteristics of the stimulating signals comprising at least one of amplitude, frequency, pulse width, pulse shape, and a phase between the pulses of the stimulating signals, and
   wherein the control unit is further configured to automatically change the phase between pulses of the stimulating signals to dynamically compensate for changes in the abnormal resting activity data.

2. The electro-stimulation device of claim 1, further comprising at least one communication unit configured to communicate with at least one additional device.

3. The electro-stimulation device of claim 2, wherein the communication unit is a primary communication unit, and wherein the sensing unit utilizes a dedicated communication unit configured to wirelessly transfer measurements to the control unit.

4. The electro-stimulation device of claim 3, wherein the control unit is a primary control unit, and wherein the sensing unit comprises a dedicated control unit such that the sensing unit is linked to the primary control unit via the dedicated communication unit and the primary communication unit.

5. The electro-stimulation device of claim 3, wherein the sensing unit is configured to process acquired data using a dedicated control unit and send resulting data to the primary control unit via a link between the dedicated communication unit and the primary communication unit.

6. The electro-stimulation device of claim 1, further comprising at least one driving circuit configured to provide power to the primary electrodes by controlling a power supply, the power being greater than a power limit of the control unit.

7. The electro-stimulation device of claim 6, wherein the stimulating signal is produced by the control unit and the stimulating signal is configured to trigger at least one driving circuit.

8. The electro-stimulation device of claim 6, further comprising a connection line which connects a connection element to the driving circuit, and wherein at least one of the at least two electrodes is detachably coupled to the connection element.

9. The electro-stimulation device of claim 8, wherein at least one of the at least two electrodes comprises a base which is received within a socket of the connection element.

10. The electro-stimulation device of claim 9, wherein at least one of the at least two electrodes and the connection element are detachably connected by a first magnet arranged on the connection element and a second magnet arranged on the at least one of the at least two electrodes.

11. The electro-stimulation device of claim 1, wherein the at least one sensing unit is configured to receive images from the patient and provide visual monitoring of the abnormal resting activities.

12. The electro-stimulation device of claim 11, wherein intensities of the abnormal resting activities are determined by the control unit by processing the received images by image processing techniques.

13. The electro-stimulation device of claim 1, wherein the at least one sensing unit comprises an accelerometer configured to sense an intensity of the at least one of tremors, rigidity and motion in a limb of the patient by measurement of acceleration of the limb attached to the sensing unit.

14. The electro-stimulation device of claim 13, wherein measurement of the at least one of tremors, rigidity and motion is conducted periodically by the control unit such that the stimulating signal is automatically adapted by the control unit to changes in a status of the patient.

15. The electro-stimulation device of claim 1, wherein the sensing unit is a signal receiver, configured to utilize the primary electrodes to receive stimulating signals passing by muscles of a patient attached to the primary electrodes.

16. The electro-stimulation device of claim 15, wherein the sensing unit is configured to sense intensities of disturbances by measuring stimulating signals passing from the muscles attached to said primary electrodes during a resting period.

17. The electro-stimulation device of claim 1, wherein the at least one remote unit is configured to change working parameters of the control unit.

18. The electro-stimulation device of claim 1, wherein measurements conducted by the sensing unit are acquirable by the remote unit.

19. The electro-stimulation device of claim 1, wherein the remote unit comprises a display unit configured to display data acquired from the control unit directly on the remote unit.

20. The electro-stimulation device of claim 1, wherein the remote unit comprises an interface, the interface being configured to provide connectivity with a terminal.

21. The electro-stimulation device of claim 20, wherein working parameters of the control unit are monitorable and changeable via said terminals.

22. The electro-stimulation device of claim 1, wherein the remote unit comprises a dedicated communication interface, the dedicated communications interface being configured to communicate with the control unit.

23. The electro-stimulation device of claim 1, wherein the stimulating signal produced by the control unit has a voltage between 0 V-15 V.

24. The electro-stimulation device of claim 1, wherein the remote unit is configured to change at least one characteristic of the stimulating signal, said characteristic of the simulating signal including at least one of amplitude, frequency, pulse width, pulse shape, and a phase between the pulses of the stimulating signal.

25. The electro-stimulation device of claim 1, wherein said electrodes are in the form of an acupuncture needle.

26. The electro-stimulation device of claim 25, wherein the acupuncture needle comprises an insulating sleeve which surrounds the acupuncture needle, and a tip which is not surrounded by the insulating sleeve.

27. The electro-stimulation device of claim 26, wherein a portion of the tip of the acupuncture needle has a thickness which is greater than a thickness of the insulating sleeve.

28. The electro-stimulation device of claim 1, wherein the electric signals sent by the primary electrodes are stimulating signals and the electric signals received by the primary electrodes are sensing signals, wherein different time slots are allocated to the sensing signals and the stimulating signals.

29. The electro-stimulation device of claim 1, wherein the control unit is configured to dynamically change a voltage and a frequency of the stimulating signal in accordance with the data received by the sensing unit from the patient.

30. The electro-stimulation device of claim 1, wherein the sensing unit comprises a camera, and intensity of the at least one of tremors, rigidity and motion is acquired from images received from the camera.

31. An electro-stimulation device adapted to stimulate at least one of a supplementary motor area, a premotor area, or a subthalmic nucleus via auricular muscles comprising:
at least two primary electrodes configured to send and receive electric signals;
at least one control unit configured to at least one of send electric signals or receive electric signals from the primary electrodes; and
a ground electrode configured to close a loop for an electrical current by providing an electrical path to a negative terminal of a power supply;
wherein each of the at least two primary electrodes comprise an acupuncture needle and an insulating sleeve which surrounds the acupuncture needle except a tip of the acupuncture needle such that the acupuncture needle is configured for insertion through an auricular skin of a patient so that the tip is embedded in the intrinsic auricular muscles of the patient and the insulating sleeve is configured for insertion into the auricular skin so that the auricular skin is insulated by the insulating sleeve from electric signals sent as stimulation signals to the tip.

32. The electro-stimulation device of claim 31, wherein a portion of the tip of the acupuncture needle has a thickness which is greater than a thickness of the insulating sleeve.

* * * * *